(12) United States Patent
Hornbostel et al.

(10) Patent No.: US 11,796,514 B2
(45) Date of Patent: Oct. 24, 2023

(54) APPARATUSES AND METHODS INVOLVING EXTRACTION OF HEAVY RARE GASES

(71) Applicant: SRI International, Menlo Park, CA (US)

(72) Inventors: Marc D. Hornbostel, Palo Alto, CA (US); Anoop Nagar, Menlo Park, CA (US); Elisabeth Perea, Menlo Park, CA (US)

(73) Assignee: SRI International, Menlo Park, CA (US)

(*) Notice: Subject to any disclaimer, the term of this patent is extended or adjusted under 35 U.S.C. 154(b) by 165 days.

(21) Appl. No.: 16/964,300

(22) PCT Filed: Jan. 24, 2019

(86) PCT No.: PCT/US2019/014947
§ 371 (c)(1),
(2) Date: Jul. 23, 2020

(87) PCT Pub. No.: WO2019/147806
PCT Pub. Date: Aug. 1, 2019

(65) Prior Publication Data
US 2021/0041405 A1  Feb. 11, 2021

Related U.S. Application Data

(60) Provisional application No. 62/621,165, filed on Jan. 24, 2018.

(51) Int. Cl.
*G01N 30/00* (2006.01)
*G01N 30/30* (2006.01)
(Continued)

(52) U.S. Cl.
CPC ........... *G01N 30/30* (2013.01); *G01N 25/488* (2013.01); *G01N 25/4826* (2013.01);
(Continued)

(58) Field of Classification Search
CPC ............... G01N 33/0036; G01N 30/00; G01N 2030/009
See application file for complete search history.

(56) References Cited

U.S. PATENT DOCUMENTS 2,698,523 A * 1/1955 Hnilicka ............... F25J 3/04412
62/925
2,793,507 A   5/1957 Hnilicka
(Continued)

FOREIGN PATENT DOCUMENTS

DE   2516243 A * 10/1975 ........... F25J 3/04745
EP   2585401 A1   5/2013
(Continued)

OTHER PUBLICATIONS

EPO. Extended European Search Report dated Dec. 10, 2020, for related European Patent Application No. 19743911.0, 13 pages.
(Continued)

*Primary Examiner* — Jamel E Williams
*Assistant Examiner* — Alex T Devito
(74) *Attorney, Agent, or Firm* — Dicke, Billig & Czaja, PLLC

(57) ABSTRACT

Embodiments in accordance with the present disclosure are directed to methods and apparatuses used for extracting heavy rare gas. An example method includes passing inlet air through an airflow path of an apparatus, removing carbon dioxide and gaseous water from the inlet air, and cooling the inlet air to a threshold temperature while passing along the airflow path. The method further includes passing the cooled inlet air through an adsorption chamber of the apparatus to adsorb heavy rare gas from the cooled inlet air while the cooled inlet air is in a gaseous state, and extracting the heavy rare gas from the adsorption chamber.

19 Claims, 6 Drawing Sheets

(51) Int. Cl.
  *G01N 25/48* (2006.01)
  *G01N 33/00* (2006.01)
  *G01N 30/02* (2006.01)
(52) U.S. Cl.
  CPC ..... *G01N 33/0022* (2013.01); *G01N 33/0036* (2013.01); *G01N 30/00* (2013.01); *G01N 2030/009* (2013.01); *G01N 2030/025* (2013.01)

(56) References Cited

U.S. PATENT DOCUMENTS

| | | | | |
|---|---|---|---|---|
| 3,063,217 | A | * | 11/1962 | Carne ................. F25J 3/04757 95/111 |
| 4,093,429 | A | * | 6/1978 | Siegler ................. B01D 53/047 95/116 |
| 4,369,048 | A | | 1/1983 | Pence |
| 5,039,500 | A | | 8/1991 | Shino et al. |
| 6,063,353 | A | | 5/2000 | Baur et al. |
| 6,286,304 | B1 | | 9/2001 | Back et al. |
| 2010/0074820 | A1 | * | 3/2010 | Kimoto ................. F25J 3/028 423/240 R |
| 2013/0112076 | A1 | * | 5/2013 | Baum ................. G01T 1/178 96/108 |
| 2016/0220943 | A1 | * | 8/2016 | Yoshikawa ............. B01J 20/06 |

FOREIGN PATENT DOCUMENTS

| | | | |
|---|---|---|---|
| GB | 1605041 | * | 5/1978 |
| RU | 2259522 C1 | * | 8/2005 |

OTHER PUBLICATIONS

V. Shkolin et al: "Thermodynamics of krypton adsorption on microporous carbon adsorbent at high pressures", Russian Chemical Bulletin, vol. 66, No. 4, Apr. 1, 2017 (Apr. 1, 2017), pp. 607-613, XP55754904, US ISSN: 1066-5285, DOI: 10.1007/s11172-017-17 80-1.

Youjin Gong et al: "Metal-organic framework derived nanoporous carbons with highly selective adsorption and separation of xenon", Journal of Materials Chemistry A, vol. 6, No. 28, Jan. 1, 2018 (Jan. 1, 2018), pp. 13696-13704, XP55754906, GB ISSN: 2050-7488, DOI: 10.1039/C8TA02091D.

Simon Stemmle: "Untersuchung Der Adsorption Von Radon Und Xenon an Verschiedenen Adsorbensien", Jan. 2013 (Jan. 1, 2013), pp. 1-62, XP055754766, retrieved from the Internet: URL:https://pure.mpg.de/rest/items/item 18 35305 3/component/file 1835680/content—[retrieved on Nov. 27, 2020].

Stefan A. Brunner: "Study of Radon Adsorption On Activated Carbon for a Purification System in Xenon", Jan. 1, 2013 (Jan. 1, 2013), pp. 1-120, XP055754762, Retrieved from the Internet: URL:https://unipub.uni -graz.at/obvugrhs/do wnload/pdf/243006?originalFilename=true [retrieved on Nov. 27, 2020].

W. F. Kenney et al: "Adsorption of Xenon On Activated Charcoal", Sep. 30, 1960 (Sep. 30, 1960), pp. 1-24, XP055754769, Retrieved from the Internet: URL:https://www.osti.gov/servlets/purl /479 4404 [retrieved on Nov. 27, 2020].

European Examination Report, mailed from the EPO dated Jan. 17, 2022, for related European Patent Application No. 19743911.0 (11 pgs.).

* cited by examiner

| | Input Air Stream | Depleted Air Stream | | |
|---|---|---|---|---|
| | | 4 hrs | 8 hrs | 21 hrs |
| Krypton (ppb) | 1000 | 710 | 780 | 720 |
| Xenon (ppb) | 90 | 34 | 51 | 55 |

APPARATUSES AND METHODS INVOLVING EXTRACTION OF HEAVY RARE GASES

CROSS-REFERENCE TO RELATED APPLICATIONS

This Utility Patent Application claims priority under 35 U.S.C. § 371 to International Application Serial No. PCT/US2019/014947, filed Jan. 24, 2019, which claims the benefit of Provisional Patent Application No. 62/621,165, filed Jan. 24, 2018; which are both incorporated herein by reference in their entirety.

OVERVIEW

Heavy rare gases, such as xenon and krypton, can be used for a variety of purposes. Xenon is the heaviest of the stable noble gases. While it is generally non-reactive, there are many potential uses, including in medical, space, and in semiconductor processing (ion etching). Medical applications include anesthesia as xenon is safer than current anesthetics, an imaging agent for lung cancer, and a protection against nerve (brain) damage in hypoxia cases and which may limit nerve damage during a stroke. Space applications include uses as ion thrusters for deep-space missions or micro-thrusters for satellite position control and in fundamental physics experiments.

These and other applications are limited by the commercial availability of heavy rare gases. The atmosphere contains large amounts of heavy rare gases but they can be extremely dilute, and therefore expensive to separate from atmospheric air.

SUMMARY OF THE INVENTION

The present invention is directed to overcoming the above-mentioned challenges and others related to extracting heavy rare gases from the air.

Various aspects of the present disclosure are directed to apparatuses and methods thereof that can be used for extracting heavy rare gases, such as xenon and krypton, from atmospheric air and while the air is in a gaseous state.

Specific embodiments are directed to a method involving passing inlet air through an airflow path of an apparatus, removing carbon dioxide and gaseous water from the inlet (e.g., atmospheric) air, and cooling the inlet air to a threshold temperature. The threshold temperature is a target temperature for adsorption of the particular heavy rare gas, and which is above a temperature at which atmospheric air transitions to a liquid state. For example, the threshold temperature can be between 80-130 Kelvin (K), 100-120 K, and/or 110 K. The cooled inlet air is passed through an adsorption chamber of the apparatus that adsorbs heavy rare gas from the cooled inlet air while the cooled inlet air is in a gaseous state, and the heavy rare gas is extracted from the adsorption chamber. In specific embodiments, a carbon-based sorbent in the adsorption chamber is used to adsorb the heavy rare gas from the cooled inlet air. The heavy rare gas is removed from the adsorption chamber by applying negative pressure to the adsorption chamber. In various embodiments, the method further includes purifying the adsorbed heavy rare gas using purifying circuitry coupled to the adsorption chamber. The purifying circuitry includes a vacuum pump configured and arranged to remove nitrogen, oxygen, argon, and neon from the adsorption chamber.

A number of embodiments can include variations and/or additional steps. For example, removing the carbon dioxide and gaseous water from the inlet air (prior to adsorbing the heavy rare gas) can include passing the inlet air, while in the gaseous state, through an air filter chamber that removes the carbon dioxide and gaseous water from the inlet air, and while the inlet air is passed at or near atmospheric pressure. In some embodiments, the cooled inlet air, with the heavy rare gas removed, is used to cool additional inlet air passing through the airflow of the apparatus. In this way, the cooled air is recycled through the apparatus and reused for cooling purposes. The recycled air, in some specific embodiments, can be cooled to a liquid state for cooling purposes when the heavy rare gas has been removed. In other embodiments and/or in addition, the heavy rare gas is extracted in response to determining the sorbent is saturated and/or above a threshold concentration. For example, the above-described method can further include determining a concentration of the heavy rare gas in the adsorption chamber and, in response to the concentration being above a threshold, extracting the heavy rare gas from the adsorption chamber. The concentration of heavy rare gas can be determined based on a flow rate and size of an adsorptive bed of the sorbent, time past, and/or signals from a sensor that measures the concentration.

Various-related and more specific embodiments are directed to an apparatus used for extracting heavy rare gas in a gaseous state. The apparatus includes an airflow path that provides movement of inlet air throughout the apparatus, an air filter chamber, heat exchange circuitry, and an adsorption chamber. The airflow path includes a plurality of interconnected channels that provide the airflow path through the apparatus. For example, the channels can be coupled or connected to an inlet port and an outlet port that respectively are used to capture or allow for the capture of inlet air from the atmosphere, and release inlet air (with carbon dioxide, gaseous water, and/or heavy rare gas removed) back to the atmosphere. The interconnected channels can be a plurality of sub-airflow paths of the airflow path, which may, as further described herein, include recirculation of cooled inlet air, with the heavy rare gas removed. The air filter chamber removes carbon dioxide and (gaseous) water from the inlet air. The air filter chamber includes an alumina and/or zeolite-based sorbent that absorbs carbon dioxide and gaseous water. The heat exchange circuitry cools the inlet air to a threshold temperature. For example, the heat exchange circuitry includes one or more heat exchangers used to cool the air. In specific embodiments, the heat exchange circuitry includes a plurality of heat exchangers and each of the heat exchangers control temperatures of the inlet air flowing through one or more of a plurality of sub-airflow paths. The adsorption chamber adsorbs heavy rare gas from the cooled inlet air while the cooled inlet air is in a gaseous state. As previously described, the adsorption chamber includes a carbon-based sorbent that adsorbs at least one of xenon and krypton.

The above-described apparatus can include a plurality of additional components. For example, the apparatus includes or is in communication with controller circuitry that controls cooling of the inlet air by the heat exchange circuitry and controls movement of inlet air and cooled inlet air throughout the apparatus. The apparatus can further include pressure circuitry (e.g., fans or other pressure sources) arranged with the airflow path to provide the movement of inlet air throughout the apparatus. In a number of related embodiments, the apparatus further includes a vacuum pump used to remove other material (e.g., nitrogen, oxygen, argon, and neon) from the adsorption chamber. For example, the heat exchange circuitry, which includes a heat exchanger, is arranged with the adsorption chamber to heat the adsorption chamber (e.g., the sorbent) and the vacuum pump is used to extract the heavy rare gas therefrom. In various additional embodiments, as described above, the airflow path recirculates the cooled inlet air, with the heavy rare gas removed, to the heat exchange circuitry for use in cooling additionally captured inlet air.

Embodiments in accordance with the present disclosure include all combinations of the recited particular embodiments. Further embodiments and the full scope of applicability of the invention will become apparent from the detailed description provided hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

Various example embodiments may be more completely understood in consideration of the following detailed description in connection with the accompanying drawings, in which.

Figure 1:
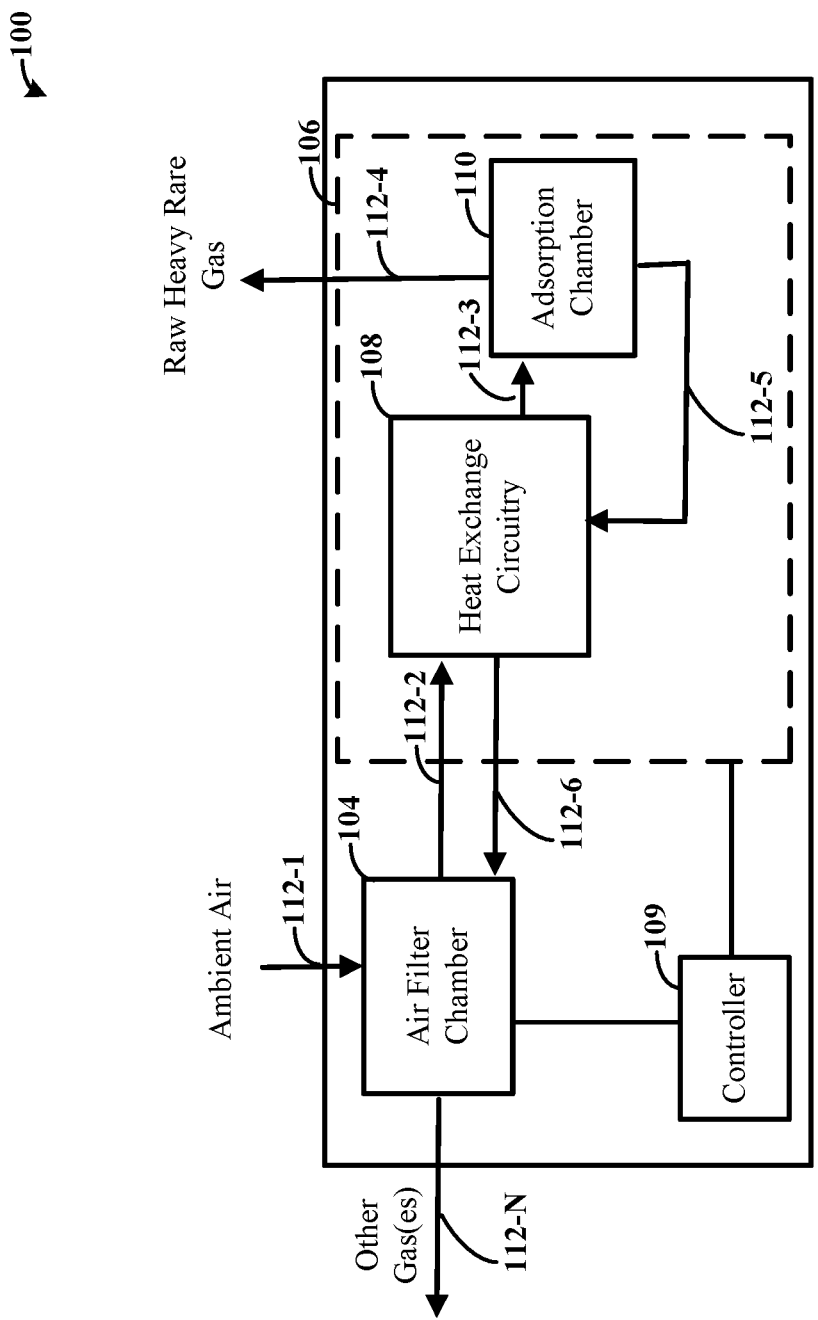
FIG. 1 illustrates an example of an apparatus, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of apparatuses and methods involving extraction of heavy rare gases. In certain implementations, the heavy rare gas is extracted from atmospheric air while the air is in a gaseous state. The heavy rare gas is extracted using a sorbent that adsorbs the heavy rare gas while the atmospheric air is in a gaseous state, is at or near atmospheric pressure and is at a threshold temperature that is ideal for adsorption. While the present invention is not necessarily limited to such applications, various aspects of the invention may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Various embodiments in accordance with the present disclosure are directed to a technique of extracting heavy rare gases from air. As previously described, the atmosphere contains large amounts of heavy rare gases, such as xenon. Heavy rare gases in atmospheric air, however, can be extremely dilute, and expensive to separate from other components of the atmospheric air. An example method for obtaining xenon, argon, krypton, and neon, is as a byproduct of cryogenic air separation for the production of oxygen. Cryogenic air separation separates the gaseous components of atmospheric air by liquefying the air and then distilling the liquid air in order to separate the major components. If the by-products are also produced, then the liquid air is diverted to a separate cryogenic distillation column to concentrate the rare gases and the remaining nitrogen and oxygen are returned to the main distillation column. The added energy used to distill the rare gases using cryogenic air separation makes the capture of xenon uneconomical if the market price of xenon is low. Embodiments in accordance with the present disclosure are directed to processes that harvest heavy rare gases, without the cost of separating the much larger quantities of oxygen, nitrogen, and argon. Such embodiments can include an adsorption-based apparatus, system and/or process operated under conditions in which heavy rare gas is adsorbed from air more (e.g., in greater concentration) than other natural components of air. The adsorption of the heavy gas can be performed using a sorbent that contains a high-surface-area carbon or carbon-based material. Moreover, the method and apparatus embodiments operate directly on atmospheric air in a gaseous state, as liquefaction and distillation of the air is not required.

The rate and/or amount of adsorption of the heavy rare gas components of gaseous ambient inlet air on the carbon material of the sorbent can be dependent on factors including the temperature at which adsorption of the heavy rare gas to be adsorbed takes place and the fraction (e.g., a relative amount or percentage) of each gas component in the inlet air. In an example xenon production process, carbon dioxide and water are first removed or "scrubbed" from the inlet air with a sorbent, such as an aluminum oxide sorbent or zeolite sorbent. The carbon dioxide and water-scrubbed air is then cooled to a target temperature (e.g., approximately 110 Kelvin (K) for xenon). The cooled air, which has the carbon dioxide and water removed, is passed through the carbon sorbent contained in an adsorption chamber, which allows heavy rare gases like xenon and/or krypton to be adsorbed. The cooled air that exits the carbon-based sorbent (e.g., xenon-depleted air) can be used to cool the inlet air, in various specific embodiments. The reuse of the cooled air can reduce the cooling demands on the apparatus. When the carbon-based sorbent is (fully or above a threshold) loaded with xenon, the air flow is stopped and the adsorption chamber is evacuated to a pressure of about 10-5 standard atmospheric pressure (atm) while the carbon sorbent remains cold. Evacuation of the adsorption chamber removes most of the nitrogen, oxygen, argon and neon from the adsorption chamber. The carbon-based sorbent is heated to near ambient temperature to allow the adsorbed xenon, and optionally some krypton co-product, to be pumped out of the adsorption chamber and collected. The resulting concentrated xenon can then be purified, resulting in the desired end product. Krypton may be produced as a by-product or discarded.

Specific embodiments in accordance with the present disclosure involve extracting heavy rare gas from ambient air by passing inlet air through an airflow path of an apparatus, removing carbon dioxide and gaseous water from the inlet air, and cooling the inlet air to a threshold temperature while passing along the airflow path. The threshold temperature can be a target temperature for adsorption of the particular heavy rare gas, and which is above a temperature at which atmospheric air transitions to a liquid state. In specific embodiments, the threshold temperature is between 80-130 K, 100-120 K, and/or 110 K. The cooled inlet air is passed through an adsorption chamber of the apparatus that adsorbs heavy rare gas from the cooled inlet air while the cooled inlet air is in a gaseous state, and the heavy rare gas is extracted from the adsorption chamber. Adsorbing the heavy rare gas from the cooled inlet air can include using a carbon-based sorbent in the adsorption chamber. The heavy rare gas is removed from the adsorption chamber by applying negative pressure to the adsorption chamber. A number of method embodiments can include various variations and/or additional steps, as further described herein.

Various embodiments are directed to an apparatus used for extracting heavy rare gas in a gaseous state. The apparatus includes an airflow path that provides movement of inlet air throughout the apparatus, an air filter chamber, heat exchange circuitry, and an adsorption chamber. The airflow path includes a plurality of interconnected channels that provide the airflow path. The channels are coupled and/or connected to an inlet port and an outlet port that are respectively used to capture or otherwise allow for the capture of inlet air from the atmosphere, and release inlet air (with carbon dioxide, gaseous water, and heavy rare gas removed) back to the atmosphere. The interconnected channels can include a plurality of sub-airflow paths of the airflow path. For example, the sub-airflow paths include a portion of the plurality of interconnected channels comprising the airflow path. The air filter chamber removes carbon dioxide and gaseous water from the inlet air. The air filter chamber includes an alumina and/or zeolite-based sorbent that absorb carbon dioxide and gaseous water. The heat exchange circuitry cools the inlet air to a threshold temperature. For example, the heat exchange circuitry includes one or more heat exchangers used to cool the air. In specific embodiments, the heat exchange circuitry includes a plurality of heat exchangers and each of the heat exchangers control temperatures of the inlet air flowing through one or more of the plurality of sub-airflow paths. The adsorption chamber adsorbs heavy rare gas from the cooled inlet air while the cooled inlet air is in a gaseous state. As previously described, the adsorption chamber includes a carbon-based sorbent that adsorbs at least one of xenon and krypton. The above-described apparatus can include a plurality of additional components, as further described herein.

The figures show example schematics for alternative implementations of the disclosed heavy rare gas extraction technology. While not specifically shown in each of the figures, it should be appreciated by one of ordinary skill that various aspects of the disclosed processes may be computer-controlled. For example, a computer system (e.g., controller circuitry) may be programmed to control the air flow through the various stages of the adsorption process, e.g., by controlling the timing and duration of opening and closing of valves that are in fluid communication with the air flow channels or lines. In various embodiments, as further described herein, one or more sensors can be placed along the airflow path to sample gases passing through, and optionally at different times, which can be used to determine a temperature of the sampled gases, if the heavy rare gas is extracted and/or not completely extracted and/or provided as feed information to the controller circuitry, as further discussed herein.

Turning now to the figures, FIG. 1 illustrates an example of an apparatus, in accordance with various embodiments. The apparatus 100 can be used to extract heavy rare gases from the air. For example, the heavy rare gas is extracted from atmospheric air and without liquefying the air for extraction.

The apparatus 100 includes an airflow path that provides movement of inlet (e.g., atmospheric or ambient) air throughout the apparatus 100. As shown, the airflow path is provided by or includes a plurality of channels 112-1, 112-2, 112-3, 112-4, 112-5, 112-6, 112-N (herein referred to generally as "the channels 112" for ease of reference). The channels 112 are interconnected and provide an airflow path through the apparatus. For example, the interconnected channels 112 can form a plurality of sub-airflow paths of the airflow path. In specific embodiments, as further described herein, the airflow path can provide recirculation of the cooled inlet air for cooling purposes. Air with the heavy rare gas removed that is reused by the apparatus 100 for cooling demands, in specific embodiments, may be liquefied for cooling additional atmospheric air and to assist in extracting heavy rare gas, although embodiments are not so limited.

In a number of embodiments, the airflow path includes and/or the channels 112 are connected to an inlet port and an outlet port. The inlet port captures inlet air from the atmosphere and is coupled to the airflow path via the channel 112-1. The outlet port, coupled to channel 112-4 (to output heavy rare gases), can release the inlet air, with the carbon dioxide, gaseous water, and/or heavy rare gas(es) removed, to the atmosphere, e.g., the surrounding environment. In various embodiments, the apparatus 100 includes a plurality of different outlet ports, such as coupled to channel 112-4 used to output the captured heavy rare gas and coupled to channel 112-N used to output other components (e.g., gaseous water, carbon dioxide, etc.) of the air. As may be appreciated, although the embodiment of FIG. 1 illustrates a single outlet port for the other gas(es) or components, embodiments are not so limited and can include more than one outlet port that outputs the other gases or components of the inlet air to the atmosphere at different portions of the airflow path.

The apparatus 100 can include an air filter chamber 104 that removes carbon dioxide and gaseous water from the inlet (e.g., atmospheric) air. In specific embodiments, the air filter chamber 104 includes one or more alumina or zeolite-based sorbents that absorb carbon dioxide and gaseous water. As may be appreciated, an alumina-based sorbent can absorb gaseous water at higher capacity than carbon dioxide and the zeolite-based sorbent can absorb carbon dioxide at higher capacity than alumina-based sorbents. Various embodiments include more than one sorbent, such as an alumina-based sorbent and a zeolite-based sorbent, that form part of the air filter chamber 104 and in other embodiments, a sorbent can include different portions that are alumina-based and that are zeolite-based and/or only includes one sorbent. The air filter chamber 104 operates at or near atmospheric pressure. As examples, the air filter chamber 104 can operate at a pressure or pressure range of 15 pounds per square inch absolute (psia), 10-20 psia, and/or 5-25 psia. As further described herein, by method embodiments provided herein, the inlet air flows through the air filter chamber 104, which removes the carbon dioxide and gaseous water, and outputs air having such components removed. The carbon dioxide and gaseous water can be output back to the atmosphere, such as via one of the output ports (e.g., as coupled to the channel 112-N), although embodiments are not so limited.

The apparatus 100 additionally includes heat exchange circuitry 108 used to cool the inlet air to a threshold temperature. The heat exchange circuitry includes one or more heat exchangers, e.g., cooling sources. Each heat exchanger can control temperatures of the inlet air flowing through one or more of the channels 112 (e.g., through the plurality of sub-airflow paths). As further described herein, the threshold temperature is a target temperature for adsorption of the heavy rare gas and above a temperature at which the inlet air transitions to a liquid state. The apparatus is used to extract heavy rare gas from atmospheric air that is in a gaseous state (and not while in or prior to being in a liquid state).

An adsorption chamber 110 adsorbs the heavy rare gas from the cooled inlet air while the cooled inlet air is in the gaseous state. The adsorption chamber 110 includes a carbon-based sorbent that adsorbs at least one of xenon and krypton.

The apparatus 100 can include various additional components. For example, the heat exchange circuitry 108, adsorption chamber 110, and various channels can be located within a cooling box 106. As may be appreciated, the apparatus 100 can further include pressure circuitry (e.g., fans or other pressure sources) arranged with the airflow path to provide the movement of inlet air throughout the apparatus 100.

In a number of embodiments, the apparatus 100 includes purifying circuitry coupled to the adsorption chamber 110. The purifying circuitry can include a vacuum pump. The purifying circuitry is used to remove nitrogen, oxygen, argon, and neon from the adsorption chamber 110 and also used to remove the heavy rare gases from the adsorption chamber 110 by applying negative pressure. For example, the vacuum pump can remove other material (e.g., nitrogen, oxygen, argon, and neon) from the adsorption chamber 110. As previously described, the heat exchange circuitry 108 includes a heat exchanger configured and arranged with the adsorption chamber 110 to heat the adsorption chamber 110 (e.g., to near ambient temperature/room temperature), and the vacuum pump extracts the heavy rare gas therefrom by applying the negative pressure. In various embodiments, the adsorption chamber 110 is heated to a temperature that is within a range of the boiling point of xenon to the boiling point of water, such as being heated to 300 K, 250-350 K, and/or 165-375 K.

The apparatus 100, in a number of embodiments, has controller circuitry 109 used to control cooling of the inlet air by the heat exchange circuitry 108 and to control movement of inlet air and cooled inlet air throughout the apparatus 100. The controller circuitry 109 includes processing circuitry and a memory circuit, and can determine when and what temperatures to cool the inlet air to, control movement of the air, and/or determine when to extract the heavy rare gas from the adsorption chamber 110. In such embodiments, the controller circuitry 109 is used to control the various components of the apparatus 100, including the pressure circuitry, heat exchange circuitry 108, and the purifying circuitry (e.g., to extract the heavy rare gas). In various embodiments, as further described herein, the controller circuitry 109 can determine when to extract the heavy rare gas, such as determining when the adsorption chamber 110 is saturated. Although the controller circuitry 109 is illustrated as part of the apparatus 100, embodiments are not so limited and part of or all of the controller circuitry can be separate from and in communication with components of the apparatus 100.

The apparatus 100 is used to extract heavy rare gas from inlet (atmospheric/ambient) air and while the air is in a gaseous state and at or near atmospheric pressure. As a specific example, the inlet air is cooled to a threshold temperature while passing along the airflow path via the heat exchange circuitry 108 and passed to the adsorption chamber 110 via the channel 112-3. The adsorption chamber 110 adsorbs heavy rare gas from the cooled inlet air while the cooled inlet air is in a gaseous state. Optionally, the cooled inlet air, with the heavy rare gas removed, is used to cool additional inlet air passing through the airflow path of the apparatus 100 via the channel 112-5 that connects the adsorption chamber 110 to the heat exchange circuitry 108. In such embodiments, the airflow path provides for recycling of the cooled air, with the heavy rare gas removed, to the heat exchange circuitry 108 for use in cooling additionally captured inlet air (e.g., recycling the air for cooling purposes, which may be cooled to a liquid state for the cooling purposes). The heavy rare gas is pumped from the sorbent in the adsorption chamber 110 using a vacuum pump and/or other pressure circuitry for extraction.

Figure 2A:
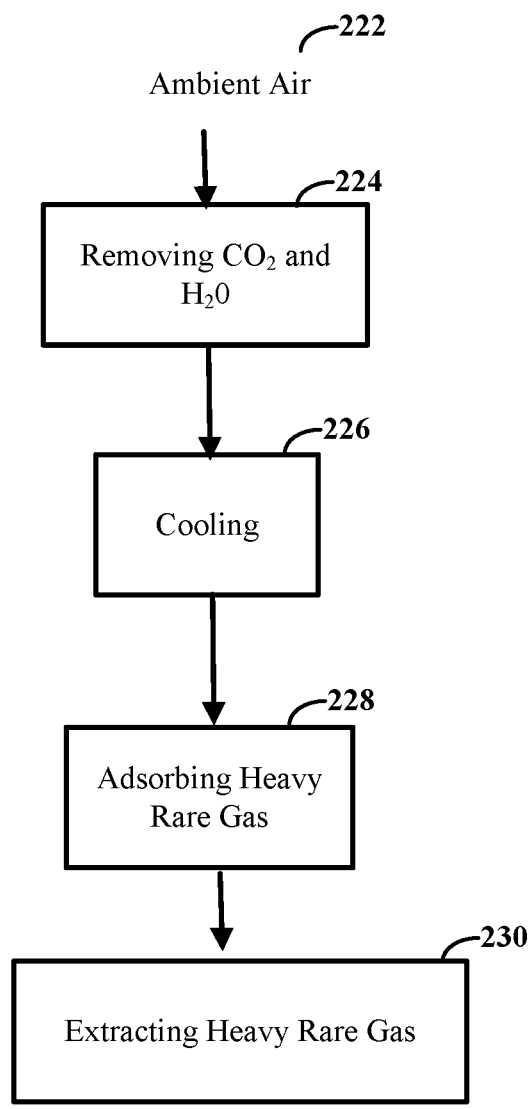
FIGS. 2A-2B illustrate example processes for extracting heavy rare gases from air, in accordance with various embodiments.
Figure 2B:
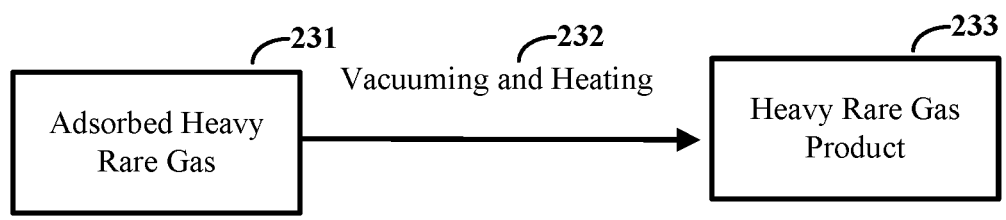

FIGS. 2A-2B illustrate example processes for extracting heavy rare gases from air, in accordance with various embodiments. More specifically, FIG. 2A illustrates an example process of extracting heavy rare gas, while not in or prior to being in a liquid state, using an apparatus, such as the apparatus 100 illustrated by FIG. 1. FIG. 2B illustrates an example process of extracting the heavy rare gas from the adsorption chamber using purifying circuitry.

As illustrated by FIG. 2A, the process can include passing inlet air 222 through an airflow path of an apparatus. At step 224, carbon dioxide and gaseous water are removed from the inlet (e.g., atmospheric) air. In specific embodiments, removing the carbon dioxide and gaseous water from the inlet air includes passing the inlet air, while in the gaseous state, through an air filter chamber that removes the carbon dioxide and gaseous water from the inlet air. The inlet air can be passed at or near atmospheric pressure.

At step 226, the process further includes cooling the inlet air to a threshold temperature while passing along the airflow path. As previously described, the threshold temperature is a target temperature for adsorption of the heavy rare gas and above a temperature at which the inlet air transitions to a liquid state. In specific embodiments, the inlet air is cooled to a temperature between 80-130 K. In further specific embodiments, the inlet air is cooled to a temperature between 100-120 K. In even further specific embodiments, the inlet air is cooled to 110 K. As described above, heat exchange circuitry can be used to cool the heavy rare gas, and in specific embodiments, the cooled inlet air with heavy rare gas removed is recycled through the apparatus for cooling purposes.

At step 228, the process includes passing the cooled inlet air through an adsorption chamber (e.g., sorbent) of the apparatus used to adsorb heavy rare gas from the cooled inlet air while the cooled inlet air is in a gaseous state. The heavy rare gas can be adsorbed from the cooled inlet air using a carbon-based sorbent in the adsorption chamber. For example, the process can include adsorbing at least one of xenon and krypton from the cooled inlet air using a sorbent in the adsorption chamber.

At step 230, the process includes extracting the heavy rare gas from the adsorption chamber. The extraction, as further described by FIG. 2B, can include removing the heavy rare gas from the adsorption chamber by applying negative pressure to the adsorption chamber. In specific embodiments, the heavy rare gas is extracted in response to determining when or that the sorbent is saturated. For example, the control circuitry can be used to determine the concentration of the heavy rare gas and/or that the sorbent is saturated. In specific embodiments, the process includes determining a concentration of the heavy rare gas in the adsorption chamber and, in response to the concentration being above a threshold, extracting the heavy rare gas from the adsorption chamber. The concentration can be determined (e.g., calculated or measured) based on a flow rate and size of the adsorptive bed of the sorbent, time past, and/or using a sensor that measures concentration, such as a time-of-flight mass spectrometer sensor, in various embodiments.

FIG. 2B illustrates a specific example of extracting heavy rare gas. As illustrated, at step 231, heavy rare gas is adsorbed by a sorbent. In various embodiments, a concentration of the adsorbed heavy rare gas is determined and the gas is extracted in response to determining the concentration is above a threshold. In response, the heavy rare gas is purified by vacuuming and heating the adsorption chamber, at step 232, and extracting the heavy rare gas product, at step 233. For example, the process can include purifying the adsorbed heavy rare gas using purifying circuitry coupled to the adsorption chamber. The purifying circuitry can include a vacuum pump that is used to remove nitrogen, oxygen, argon, and neon from the adsorption chamber and/or a heat exchanger, as previously described.

Figure 3:
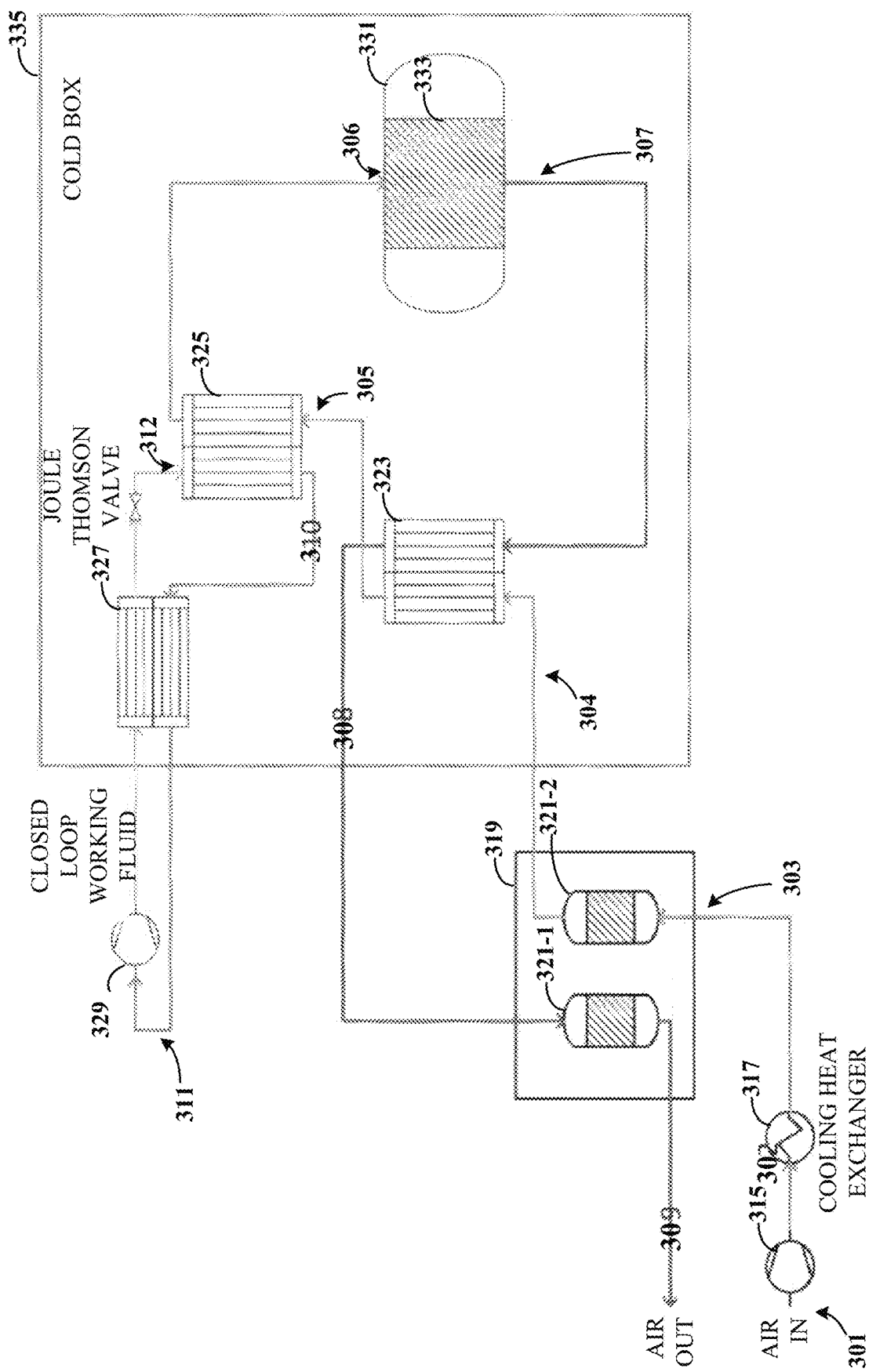
FIG. 3 illustrates another example apparatus, in accordance with various embodiments.

FIG. 3 illustrates another example apparatus, in accordance with various embodiments. Ambient inlet air (gaseous) enters the apparatus, at step 301. A compressor 315 compresses the air, heating it. The heated compressed air is cooled by a heat exchanger 317, at step 302. This heating and cooling process removes water from the inlet air. At step 303, the cooled air with water removed, enters an air filter chamber 319 (which includes air scrubbers 321-1, 321-2) in which an alumina- or zeolite-based sorbent (e.g., air scrubber 321-2) is used to remove the carbon dioxide and residual water from the air. In various embodiments, different components of the air filter chamber 319 are used to remove carbon dioxide and residual water from different channels. For instance, air scrubber 321-2 can be used to remove the carbon dioxide and residual water from air from the cooling heat exchanger 317, and air scrubber 321-1 can be used to remove the carbon dioxide and residual water from air from the heat recovery heat exchanger 323 (as discussed below). At step 304, the air with water and carbon dioxide removed is at a temperature of, in the case of xenon, about 298 K, although embodiments are not so limited. This air enters a heat recovery heat exchanger 323, which cools the air a first amount, such that the air is at a temperature that is just above the target adsorption temperature (e.g., 112 K for xenon). At step 305, the cooled air enters the main cooling step or circuit, which illustratively includes another heat exchanger 325 fluidically coupled with a refrigeration circuit. The refrigeration circuit is associated with the fluid loop (e.g., at step 311), and includes the heat exchangers 325, 327 and the compressor 329. Operation of the main cooling circuit (e.g., the heat exchanger 325) can be computer controlled using control circuitry (e.g., logic) configured to reduce the temperature of the air that enters, at the step 305, to the threshold or target temperature for adsorption of the gas component desired to be extracted from the air (e.g., in the range of about 110 K, for xenon). The air, now cooled to the target temperature, enters the adsorption chamber 331, at step 306, where the xenon is extracted using a carbon or carbon-based sorbent 333. At step 307, the air with the target gas component (e.g., xenon) removed exits the adsorption chamber 331 and, optionally, is circulated back to the heat recovery heat exchanger 323 for re-use to help cool additional incoming air that enters the heat recovery heat exchanger 323, at step 304. This re-used air exits the heat recovery heat exchanger 323, at step 308, and passes through an air scrubber 321-1 before exiting the apparatus, at step 309. The adsorbed heavy rare gas (e.g., xenon) can be captured and delivered for use by one or more of the applications once a threshold (e.g., enough) amount of the heavy rare gas is collected in the sorbent 333. The cooling and refrigeration circuits, as well as the adsorption chamber 331, are housed in a cooling box 335. Other components of the apparatus may be located outside of the cooling box 335 (e.g., a cold box).

More specifically, in various embodiments, a closed loop fluid system can be used to cool the inlet air. In such a closed loop fluid system, the cooling box 335 is sealed. The closed loop fluid system can use cooled fluid that is flowed through a flow path provided by one or more channels coupled to components of the loop, such as the illustrated compressor 329 and heat exchanger 327 and, optionally, another cooling heat exchanger (which may be located between the compressor 329 and the heat recovery heat exchanger 327, similar to the cooling heat exchanger 317). At step 312, fluid is used to cool the inlet air via the heat exchanger 325, which exits and is circulated back to the heat recovery heat exchanger 327 for re-use for further cooling purposes, at step 310. The fluid enters the compressor 329, at step 311, which compresses the fluid, heating it. The heated compressed fluid can be cooled by another heat exchanger (not illustrated but similar to 317). The cooled fluid is further cooled by the heat recovery heat exchanger 327 and the cooled fluid enters, at step 312, the main cooling step or circuit (e.g., the heat exchanger 325) and is used to cool the inlet air that enters the enters the main cooling step or circuit, at step 305. For example, the working fluid is allowed to expand through the Joule Thomson valve, causing the pressure and temperature to decrease. The cold working fluid (at step 312) is then used to cool the air (at step 305) in the heat exchanger 325.

As illustrated by the specific embodiment of FIG. 3, the heat exchange circuitry of the apparatus can include a variety of components. Although the specific apparatus of FIG. 3 illustrates three separate components as the heat exchange circuitry, e.g., the two heat exchangers 323, 327 and the heat exchanger 325 (e.g., the main cooling circuit), embodiments are not so limited and can include more or less components, such as a single heat exchange circuit or apparatus can be used to provide the functionality of the three separate components. In other embodiments, additional circuitry can be used.

Figure 4:
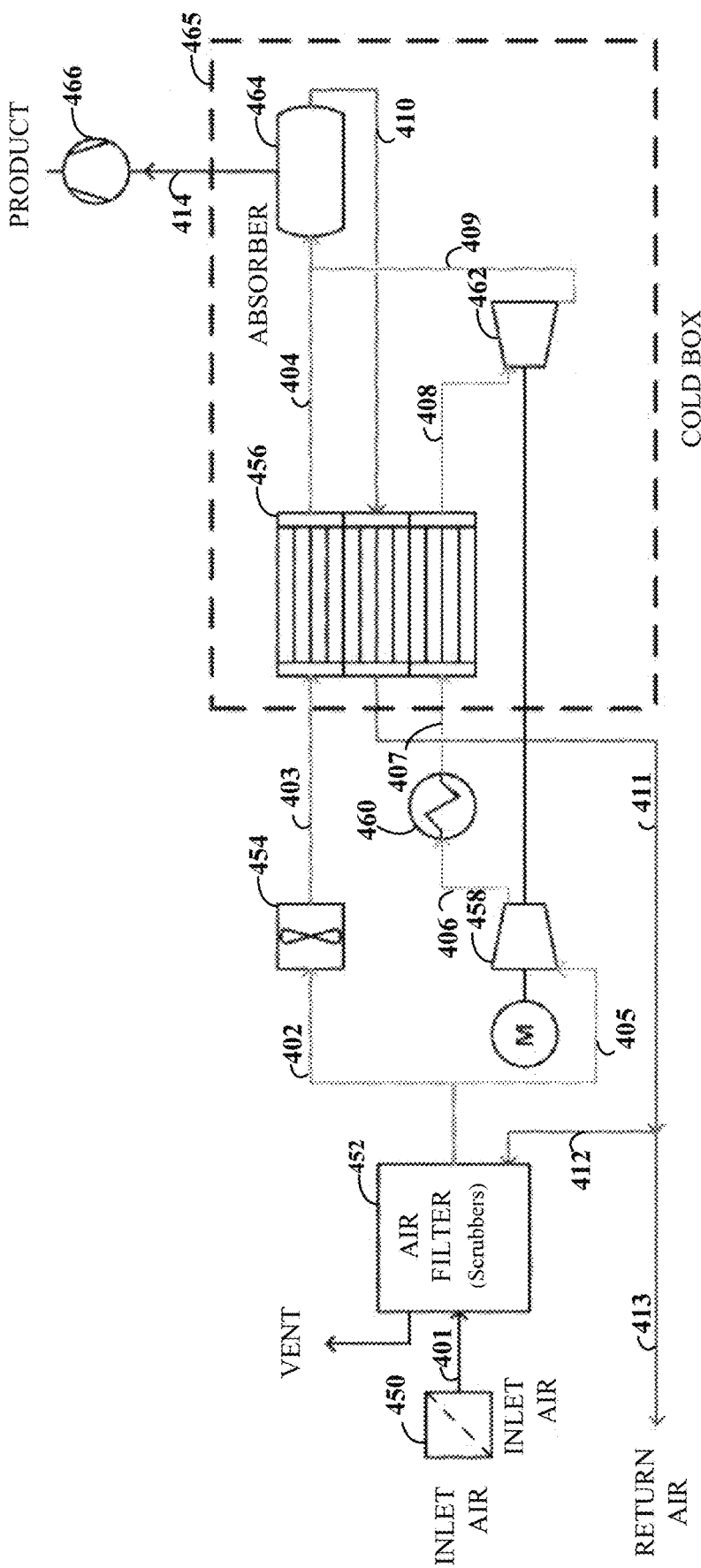
FIG. 4 illustrates another example apparatus, in accordance with various embodiments.

FIG. 4 illustrates another example apparatus, in accordance with various embodiments. More specifically, FIG. 4 illustrates an alternative version of an example apparatus that includes a cooling mechanism that may be more efficient than the apparatus illustrated by FIG. 3. Inlet ambient (gaseous) air passes through an inlet filter 450 and enters an air filter chamber 452, at step 401. As may be appreciated, the air filter chamber 452 includes air scrubbers, such as a carbon dioxide scrubber. The airstream exiting the air scrubber with carbon dioxide and water removed is divided (e.g., by baffles or a flow meter) into a first airstream (e.g., line or channel at step 402) and a second airstream (e.g., line or channel at step 405) which are connected in parallel. A low pressure (e.g., less than 5 pounds per square inch (psi)) fan 454 pulls the first air stream, at step 402 (e.g., via a channel), into a heat exchanger 456 through another channel (e.g., line), at step 403. The first air stream entering the heat exchanger 456 through the channel, at step 403, is near ambient temperature. Separately, and/or concurrently, a high (e.g., 15 psi) compressor 458 causes the smaller-volume second air stream to enter the compressor, at step 405, which increases the temperature of the second air stream. The heated air of the second air stream flows from the compressor 458 to a cooling circuit (e.g., cooling heat exchanger) 460, at step 406, before the second airstream enters the heat exchanger 456, at step 407. The operation of the fan 454 and the compressor 458 can be configured manually or computer controlled, such as by controller circuitry, to establish the relative volumes of the first and second air streams, as well as the pressure changes caused by those devices. In some embodiments, the first and second air streams are at a ratio of 15:1, although embodiments are not so limited and can include various ratios. For example, the ratio of the first and second air streams can be adjusted to adjust the amount of cooling and which is used to maintain a target temperature. A smaller ratio, e.g., 14:1, provides more cooling and a larger ratio, e.g., 16:1, provides less cooling. In specific embodiments, the ratio is adjusted continuously by the control circuitry to control the temperature of the combined air in the adsorption chamber 464. In more-specific and related embodiments, one or more temperature sensors can be located within the airflow path, and which provide temperature readings (such as at step 409) as feedback to the control circuitry. At step 404, the air of the first airstream exits the heat exchanger 456 at a cryogenic temperature (e.g., 112 K) which may not be the target temperature for adsorption of the desired heavy rare gas. At step 408, the air of the second airstream exits the heat exchanger 456 and is cooled by a turbo expander 462 to a temperature that is just above the boiling point of the air stream (e.g., around 80 K). The airline or channel, at step 409, connects with the airline or channel, at step 404, so as to mix the two airstreams (e.g., mix the first stream at 112 K with the second stream at 80 K). In this way, the parallel processing of the second air stream helps cool the main, first airstream, to the desired target temperature for adsorption of the desired gas component of the air (e.g., 110 K, for xenon). At step 410, xenon-depleted air is re-circulated to assist with cooling of incoming air at steps 410, 411, 412, and then returned to the atmosphere, at step 413. The mixture of the first and second air streams from steps 404 and 409 enters the adsorption chamber 464, where the desired heavy rare gas is adsorbed using a carbon or carbon-based sorbent.

Once the sorbent is full of the extracted gas (e.g., xenon), the extracted heavy rare gas can be collected and used for any number of applications including any of the applications mentioned above (e.g., medical, space, semiconductors). For example, a vacuum pump 466 can be used to pump the extracted xenon out of the adsorption chamber to produce the final extracted product, at step 414. One or more sensors may be placed in or on the adsorption chamber 464 and/or sorbent in order to sense when the adsorbed gas is ready to be pumped out. As such, the operation of the vacuum pump 466 may be computer-controlled based on the sensor readings. In the specific embodiment of FIG. 4, the cooling (e.g., cold) box 465 houses various components, such as the heat exchanger 456, turbo expander 462 and adsorption chamber 464, and other components of the system may be located outside of the cooling box 465.

The various embodiments can be used to extract heavy rare gases which can be used for a variety of uses. Many uses of xenon or other heavy rare gases have been abandoned due to the limited availability of the desired gas component and the difficulty of adding new production capacity for the desired gas component. For example, because xenon is currently only produced as a by-product of oxygen production, it is not economical to add new xenon production capacity. The disclosed embodiments allow for scalable production of xenon, thereby enabling new applications of xenon that may otherwise overload the global xenon production capacity. Additionally, embodiments in accordance with the present disclosure allow for extracting heavy rare gas from ambient air while the air is at or near atmospheric pressure and is in gaseous state.

MORE DETAILED/EXPERIMENTAL EMBODIMENTS

Embodiments in accordance with the present disclosure include apparatuses and methods involving extraction of heavy rare gases from atmospheric air. The heavy rare gas is, somewhat surprisingly, extracted while the inlet air is at or near atmospheric pressure and in a gaseous state (e.g., not in a liquid state for extracting). As may be appreciated, inlet air that is already cooled and has the heavy rare gas removed can be recycled through the apparatus to cool additional inlet air and for extracting additional heavy rare gas. Various specific apparatuses can be used to extract the heavy rare gas, which can have a variety of different components and features used to pass inlet ambient air, such as different components and orders of components than illustrated by the various figures herein.

Figures 5A, 5B:
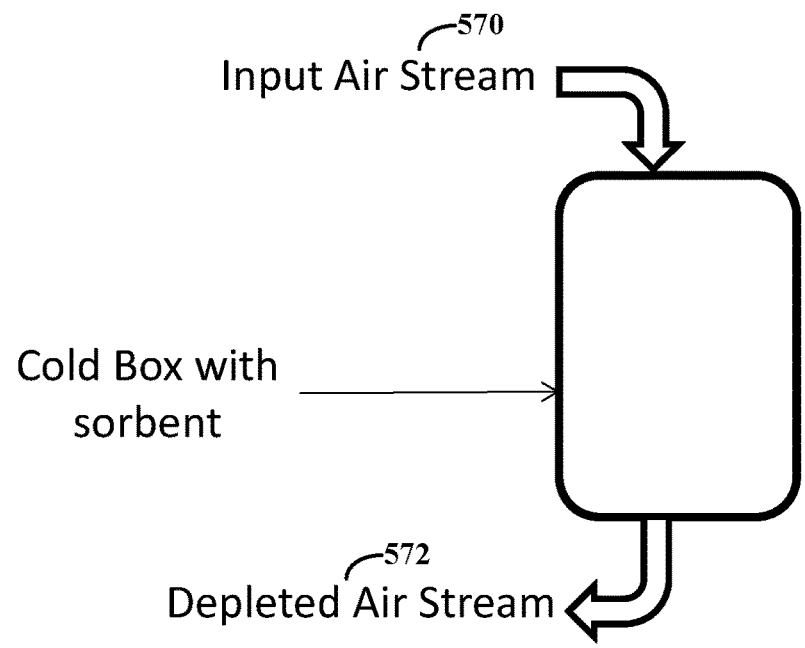
FIGS. 5A-5B illustrate an example of processing ambient air to extract heavy rare gases, in accordance with various embodiments.

FIGS. 5A-5B illustrate an example of processing ambient air to extract heavy rare gases, in accordance with various embodiments. As shown by FIG. 5A, inlet ambient air 570 is used to obtain heavy rare gases by removing water and carbon dioxide from the air using an activated alumina to absorb the same. The incoming air is then cooled to around 110 K and passed through a sorbent. Samples of the depleted air stream 572 are collected and analyzed for heavy rare gases using time-of-flight mass spectrometry. As shown by FIG. 5B, the amounts of heavy rare gas in the depleted air stream are lower than the input air stream, which illustrates the extraction of the heavy rare gas from ambient air.

As used herein, heavy rare gas includes or refers to rare gas, sometimes referred to as noble or inert gases, with an atomic weight greater than 40. Example heavy rare gases include krypton and xenon. The apparatus, as described above, is used to extract heavy rare gas from air that not in or prior to being in a liquid state, is at or near atmospheric pressure, and at a threshold temperature by flowing inlet air through an airflow path. Ambient air includes or refers to atmospheric air, e.g., in a natural state and/or that is or near atmospheric pressure. Ambient air contains a variable amount of gaseous water. The dry portion of ambient air is typically seventy-eight percent nitrogen and twenty-one percent oxygen. The extra one percent is made up of a combination of carbon dioxide, helium, methane, argon and hydrogen. Atmospheric air includes or refers to air which is prevailing under atmospheric conditions. Atmospheric conditions are different for different locations and patterns of wind. At or near atmospheric pressure includes or refers to the pressure by the weight of the atmosphere, which can vary with altitude. A threshold temperature for cooling the air includes or refers to a target temperature for adsorption of the particular heavy gas. The threshold temperature is above a temperature at which air transitions to a liquid state and, in specific embodiments, is between 80-130 K, 100-120 K, and/or is 110 K. The airflow path includes or is otherwise formed by a plurality of channels that are interconnected to one another (directly or through other components of the apparatus). The channels include or refer to a passage for air or fluid, such a pipe, a line, a tubing, or other type of passageway. In some instances, the channels are interchangeably referred to as airlines herein. The channels can be a variety of shapes, sizes, and formed of a variety of material, such as plastic, rubber, metal, ceramics, glass, etc. An adsorption chamber includes or refers to a chamber having a sorbent that adsorbs heavy rare gas(es) from inlet air. The sorbent can be a charcoal-based sorbent, in specific embodiments. The air filter chamber includes or refers to a chamber having one or more filters used to remove carbon dioxide and gaseous water from inlet air. The filters, which are sometimes herein referred to as air scrubbers, include or refer to sorbents used to remove carbon dioxide and gaseous water from the air and while the air is at or near atmospheric pressure, such as the above described alumina or zeolite-based sorbents. A sorbent includes or refers to a substance or material having the property of collecting molecules of another substance by sorption. A sorbent can absorb or adsorb liquids and/or gases. Heat exchange circuitry includes circuitry used to cool a temperature of gases (e.g., air) or liquid in the apparatus, such as one or more cooling heat exchangers and/or heat recovery heat exchangers, compressors, refrigeration or cooling circuits, and other components. Heat exchangers, as used herein, include or refers to circuitry that transfers heat between two or more fluids or gases. As may be appreciated, the fluids or gases can be separated to prevent mixing or can be in direct contact. Examples of heat exchangers can include shell-and-tube and plate/fin heat exchangers. A cooling box, sometimes interchangeably referred to as a cold box, includes or refers to a container formed of or including a material that mitigates changes in or otherwise maintains internal temperature of the container.

The controller circuitry includes or refers to one or more computer circuits, including processing circuitry and memory circuitry for storing and accessing a program to be executed as a set (or sets) of instructions (and/or to be used as configuration data to define how the programmable circuit is to perform). For example, the controller circuitry can include or otherwise have access to computer-readable instructions stored on memory that includes instructions for controlling the airflow, temperature, determining gas concentration, and/or otherwise controlling the other components of the apparatus (e.g., heat exchangers, pressure sources, compressors, inlet/output ports), that when executed by the processor circuitry of the controller circuitry is used to control the extraction of heavy rare gas from ambient air. For example, when executed, the computer-readable instructions are used to control cooling and flow of inlet air throughout the apparatus, identify when the sorbent of the adsorption chamber is saturated or otherwise is to be evacuated, and to control extraction of the heavy rare gas from the sorbent. Pressure circuitry includes or refers to hardware components that provide or otherwise direct the movement of air. Example pressure circuitry includes fans, vacuum pumps, compressors, etc. Purifying circuitry includes or refers to hardware circuitry used to remove material (e.g., nitrogen, oxygen, argon, and neon) from the adsorption chamber, such as a vacuum pump or fan and, optionally, a heat exchanger. Vacuum pump includes or refer to hardware that removes (gas) molecules from a volume, such as chamber or channel, in order to provide a partial vacuum. A port includes or refers to hardware or physical component that is used to capture inlet air from the atmosphere and is coupled to the airflow path, such as a channel with an opening that is exposed to the atmosphere. A sensor includes or refers to circuitry that detects or measures a physical property and provides an indication or otherwise responds to the physical property.

The skilled artisan would recognize that various terminology as used in the Specification (including claims) connote a plain meaning in the art unless otherwise indicated. As examples, the Specification describes and/or illustrates aspects useful for implementing the claimed disclosure by way of various circuits or circuitry which may be illustrated as or using terms such as blocks, modules, device, system, unit, controller, and/or other circuit-type depictions (e.g., reference numerals 108 and 109 of FIG. 1 depict a block/module as described herein). Such circuits or circuitry are used together with other elements to exemplify how certain embodiments may be carried out in the form or structures, steps, functions, operations, activities, etc. For example, in certain of the above-discussed embodiments, one or more modules are discrete logic circuits or programmable logic circuits configured and arranged for implementing these operations/activities, as may be carried out in the approaches shown in FIG. 3-4. In certain embodiments, such a programmable circuit is one or more computer circuits, including memory circuitry for storing and accessing a program to be executed as a set (or sets) of instructions (and/or to be used as configuration data to define how the programmable circuit is to perform), and an algorithm or process as described at FIGS. 2A-2B is used by the programmable circuit to perform the related steps, functions, operations, activities, etc. Depending on the application, the instructions (and/or configuration data) can be configured for implementation in logic circuitry, with the instructions (whether characterized in the form of object code, firmware or software) stored in and accessible from a memory (circuit).

Various embodiments described above, may be implemented together and/or in other manners. One or more of the items depicted in the present disclosure can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

What is claimed is:
1. A method, comprising:
   passing inlet ambient air from the atmosphere through an airflow path of an apparatus;
   removing carbon dioxide and gaseous water from the inlet ambient air using at least one sorbent in an air filter chamber of the apparatus, wherein the at least one sorbent is selected from an alumina-based sorbent and a zeolite-based sorbent;
   cooling the inlet ambient air, with the carbon dioxide and gaseous water removed, to a threshold temperature of between 100-120 Kelvin while passing the inlet ambi- ent air along the airflow path from the air filter chamber to an adsorption chamber of the apparatus;

passing the cooled inlet ambient air, as cooled to the threshold temperature, into and through the adsorption chamber of the apparatus that includes a carbon-based sorbent configured and arranged to adsorb xenon gas from the cooled inlet ambient air at a greater concentration than other components remaining in the inlet ambient air and while the cooled inlet ambient air is in a gaseous state; and extracting the xenon gas from the adsorption chamber to produce an end product of the xenon gas by heating the adsorption chamber and pumping the xenon gas out of the adsorption.

2. The method of claim 1, further including:

absorbing the carbon dioxide and gaseous water from the inlet ambient air using the at least one sorbent and while the inlet ambient air is at or near atmospheric pressure;

wherein the other components remaining in the inlet ambient air include at least nitrogen and oxygen; and removing at least some of the other components from the adsorption chamber using purifying circuitry coupled to the adsorption chamber by pumping the other components from the adsorption chamber to the atmosphere while the xenon gas is adsorbed by the carbon-based sorbent and cooled to the threshold temperature.

3. The method of claim 1, further including:

adsorbing krypton gas from the cooled inlet ambient air using the carbon-based sorbent in the adsorption chamber and while the inlet ambient air is cooled to the threshold temperature of between 100-120 Kelvin; and extracting at least the xenon gas from the adsorption chamber to produce the end product of the xenon gas by heating the adsorption chamber to a temperature of between 165-375 Kevin.

4. The method of claim 1, further including:

purifying the adsorbed xenon gas using purifying circuitry coupled to the adsorption chamber, the purifying circuitry including a vacuum pump configured and arranged to remove the other components including at least nitrogen, oxygen, argon, and neon, which remain in the inlet ambient air after the xenon gas is adsorbed, from the adsorption chamber by pumping the nitrogen, oxygen, argon, and neon from the adsorption chamber to the atmosphere via application of negative pressure to the adsorption chamber by the vacuum pump and while the xenon gas is adsorbed by the carbon-based sorbent and cooled to the threshold temperature, and after purifying the adsorbed xenon gas, heating the adsorption chamber to a temperature within range of a boiling point of xenon and a boiling point of water and pumping the xenon gas out of the adsorption chamber via application of negative pressure to the adsorption chamber by the vacuum pump.

5. The method of claim 1, wherein cooling the inlet ambient air includes cooling to the temperature between 100-120 Kelvin using heat exchange circuitry of the apparatus.

6. The method of claim 1, wherein cooling the inlet ambient air includes cooling to 110 Kelvin.

7. The method of claim 1, wherein removing the carbon dioxide and gaseous water from the inlet ambient air further includes passing the inlet ambient air, while in the gaseous state and while at atmospheric pressure and temperature, through the air filter chamber of the apparatus, the air filter chamber configured and arranged to remove the carbon dioxide and gaseous water from the inlet ambient air.

8. The method of claim 1, further including determining a concentration of the xenon gas in the adsorption chamber and, in response to the concentration being above a threshold and associated with the carbon-based sorbent being saturated, extracting the xenon gas from the adsorption chamber to produce the end product of the xenon gas.

9. The method of claim 1, wherein the xenon gas is removed from the adsorption chamber by heating the adsorption chamber to a temperature between 250-350 Kelvin and then pumping the xenon gas out by applying negative pressure to the adsorption chamber via a vacuum pump coupled to the adsorption chamber to produce the end product of the xenon gas.

10. The method of claim 1, wherein the xenon gas is removed from the adsorption chamber by heating the adsorption chamber to a temperature between 165-375 Kelvin and then pumping the xenon gas out by applying negative pressure to the adsorption chamber to extract the xenon gas therefrom.

11. The method of claim 1, further including using the cooled inlet ambient air, with the xenon gas removed, to cool additional inlet ambient air passing through the airflow path of the apparatus.

12. An apparatus, comprising:

an airflow path configured and arranged to provide movement of inlet ambient air from the atmosphere into and through the apparatus;

an air filter chamber including at least one sorbent configured and arranged to remove carbon dioxide and gaseous water from the inlet ambient air via absorption by the at least one sorbent and while at or near atmospheric pressure, wherein the at least one sorbent is selected from an alumina-based sorbent and a zeolite-based sorbent;

heat exchange circuitry configured and arranged to cool the inlet ambient air, with the carbon dioxide and gaseous water removed, to a threshold temperature of between 100-120 Kelvin while the inlet ambient air is passed along the airflow path from the air filter chamber into an adsorption chamber of the apparatus;

the adsorption chamber including a carbon-based sorbent configured and arranged to adsorb xenon gas from the cooled inlet ambient air at a higher concentration than other components remaining in the cooled inlet ambient air and while the cooled inlet ambient air is in a gaseous state and while at or near atmospheric pressure; and a vacuum pump and at least a portion of the heat exchange circuitry configured and arranged with the adsorption chamber to apply heat to the adsorption chamber and to pump the xenon gas out of the adsorption chamber to extract the xenon therefrom to produce an end product of the xenon gas.

13. The apparatus of claim 12, further including controller circuitry configured and arranged to control cooling of the inlet ambient air by the heat exchange circuitry and to control movement of inlet ambient air and cooled inlet ambient air into the apparatus from the atmosphere and throughout the apparatus.

14. The apparatus of claim 12, wherein the airflow path includes a plurality of interconnected channels configured and arranged to provide an airflow path through the apparatus, the airflow path including recirculation of the cooled inlet ambient air, with the xenon gas removed, to the heat exchange circuitry for use in cooling additionally captured inlet ambient air.

15. The apparatus of claim 12, wherein the vacuum pump is configured and arranged to remove other material from the adsorption chamber; and wherein the heat exchange circuitry includes a heat exchanger configured and arranged with the adsorption chamber to heat the adsorption chamber and the vacuum pump is configured and arranged to pump the xenon gas out by application of negative pressure, after application of the heat, and to extract the xenon gas therefrom.

16. The apparatus of claim 12, wherein:

the carbon-based sorbent is further configured and arranged to adsorb krypton gas from the cooled inlet ambient as cooled to the threshold temperature of between 100-120 Kelvin and while at or near atmospheric pressure.

17. The apparatus of claim 12, further including pressure circuitry configured and arranged with the airflow path to provide the movement of inlet ambient air throughout the apparatus, wherein the vacuum pump is further configured with the adsorption chamber to remove at least some of the other components remaining in the inlet ambient air from the adsorption chamber while the xenon is adsorbed by the carbon-based sorbent.

18. The apparatus of claim 12, further including:

an inlet port configured and arranged to capture inlet ambient air from the atmosphere and coupled to the airflow path; and an outlet port configured and arranged to release the inlet ambient air, with the carbon dioxide, gaseous water, and xenon gas removed, back to the atmosphere.

19. The apparatus of claim 12, wherein the airflow path includes a plurality of interconnected channels that form a plurality of sub-airflow paths of the airflow path, and the heat exchange circuitry includes a plurality of heat exchangers, each of the plurality of heat exchangers configured and arranged to control temperatures of the inlet ambient air flowing through one or more of the plurality of sub-airflow paths.

* * * * *